United States Patent [19]
Glowa et al.

[11] Patent Number: 5,592,727
[45] Date of Patent: Jan. 14, 1997

[54] METHOD OF MAKING ARTHROSCOPIC SHAVER WITH ROTATABLE COLLET AND SLIDE ASPIRATION CONTROL VALVE

[75] Inventors: Michael P. Glowa; Phillip J. Berman, both of St. Petersburg; Dale Slenker, Palm Harbor, all of Fla.

[73] Assignee: Linvatec Corporation, Largo, Fla.

[21] Appl. No.: 542,204

[22] Filed: Oct. 12, 1995

Related U.S. Application Data

[62] Division of Ser. No. 303,910, Sep. 9, 1994, Pat. No. 5,492,527.

[51] Int. Cl.$^6$ ........................................... B23P 11/00
[52] U.S. Cl. ............................................. 29/434; 29/527.1
[58] Field of Search ................................... 29/434, 527.1; 72/253.1, 257; 264/176.1, 177.1, 209.1

[56] References Cited

U.S. PATENT DOCUMENTS

| | | |
|---|---|---|
| Re. 34,556 | 3/1994 | Sjostrom et al. . |
| 3,223,088 | 12/1965 | Barber et al. . |
| 3,618,611 | 11/1971 | Urban . |
| 3,835,858 | 9/1974 | Hagen . |
| 3,847,154 | 11/1974 | Nordin . |
| 4,014,342 | 3/1977 | Staub et al. . |
| 4,071,029 | 1/1978 | Richmond et al. . |
| 4,674,502 | 6/1987 | Imonti . |
| 5,112,299 | 5/1992 | Pascaloff . |
| 5,123,904 | 6/1992 | Shimomura . |
| 5,133,729 | 7/1992 | Sjostrom . |
| 5,217,478 | 6/1993 | Rexroth . |
| 5,286,253 | 2/1994 | Fucci . |
| 5,352,234 | 10/1994 | Scott . |
| 5,376,078 | 12/1994 | Dinger, III et al. . |

FOREIGN PATENT DOCUMENTS

| | | |
|---|---|---|
| 1349881 | 4/1974 | United Kingdom . |

OTHER PUBLICATIONS

"The Switch Is On." Pacesetter 3500 Arthroscopic Surgical System, Dyonics, Inc. Feb. 1988, 6 pages.
Linvatec 1994 Product Catalog, Intraarc Arthroscopy Power System, 5 pages.

Primary Examiner—David P. Bryant
Attorney, Agent, or Firm—Gene Warzecha

[57] ABSTRACT

A rotatable surgical shaver handpiece having a rotating elongated inner member within a fixed outer member is provided with a means for varying the cutting window orientation of the outer tubular member. The window orientation is adjusted by providing a rotatable collet assembly which has a hollow, outer, longitudinally movable body to which the outer hub member is keyed. The outer collet member is concentrically situated about an inner collet body and is fixed to an annular, toothed locking surface which is movably biased against an identical toothed locking surface fixed to the inner collet body. The teeth have sloped sides and are shallow such that the pre-loaded force compressing the two locking surfaces together is easily overcome by rotating the outer collet body to cause the teeth of one locking surface to slide along the teeth of the mating locking surface. In another embodiment, the invention is provided with a blade recognition means for identifying a code associated with a particular blade assembly regardless of the window orientation of the outer tubular member of the blade assembly. In another embodiment of the invention the handpiece is provided with an extruded body fitted with a longitudinally slidable aspiration control switch.

2 Claims, 15 Drawing Sheets

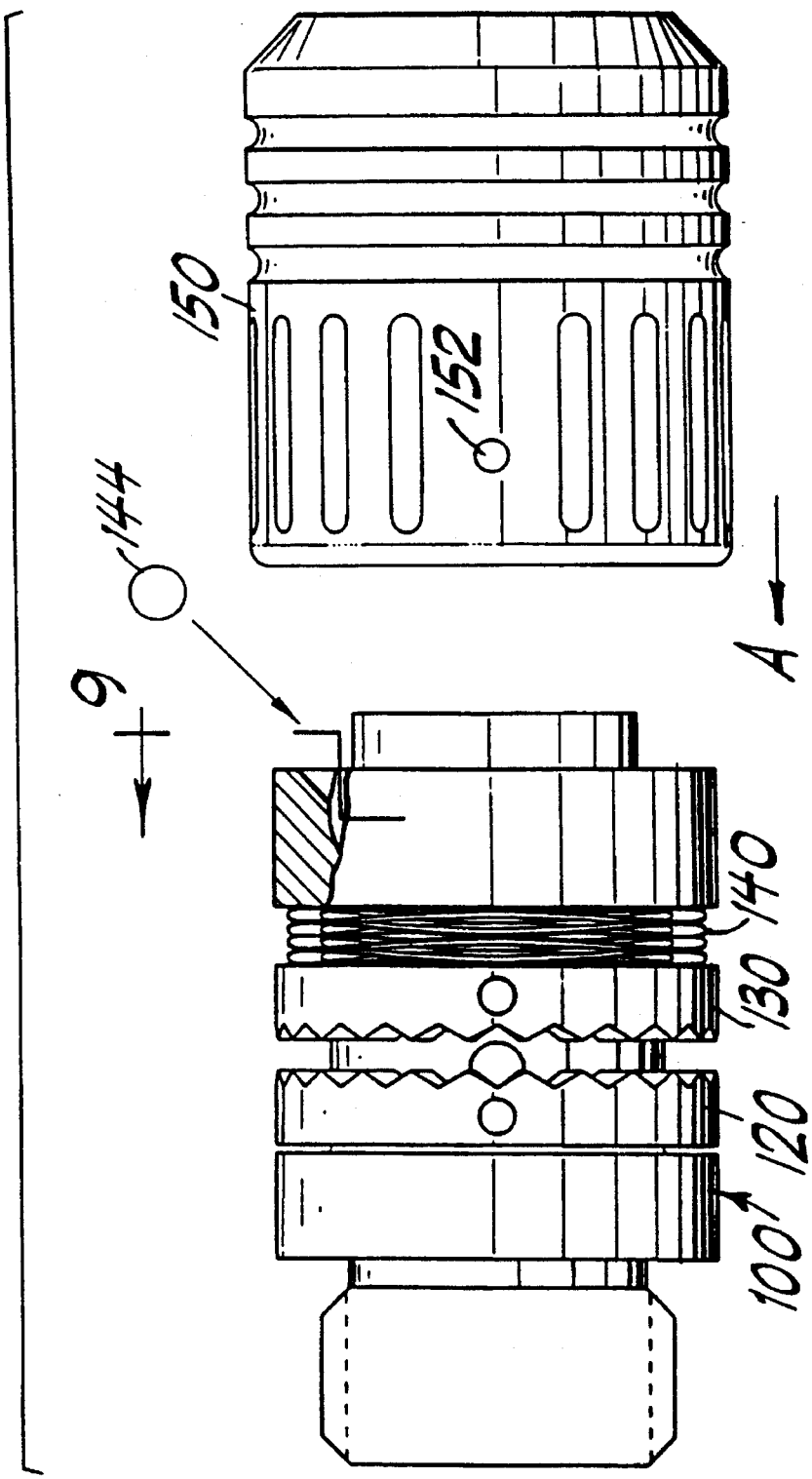

METHOD OF MAKING ARTHROSCOPIC SHAVER WITH ROTATABLE COLLET AND SLIDE ASPIRATION CONTROL VALVE

This is a divisional application of U.S. Ser. No. 08/303,910, filed Sep. 9, 1994, now U.S. Pat. No. 5,492,527, granted Feb. 20, 1996.

BACKGROUND OF THE INVENTION

1. Field of the Invention

This invention relates to a surgical handpiece for use during endoscopic surgical procedures for driving an elongated rotatable surgical instrument and aspirating material from the surgical work site. More particularly, this invention relates to a method for manufacturing the handpiece and a means for enabling the orientation of the instrument attached to the handpiece to be angularly adjusted relative to the axis of the handpiece. The invention also relates to a surgical handpiece having a novel, longitudinally activated aspiration control valve.

2. Description of the Prior Art

Surgical handpieces have long been used to house the mechanical and electrical components necessary to operate a variety of powered surgical instruments attached to the handpiece. While some such instruments are used in open surgical procedures, the use of surgical cutting instruments has also become well accepted in performing closed surgery such as arthroscopic or more generally endoscopic surgery. The terms "arthroscopic" and "endoscopic" may be used interchangeably herein and are intended to encompass arthroscopic, endoscopic, laparoscopic, hysteroscopic or any other similar surgical procedures performed with elongated instruments inserted through small openings in the body. In such surgery, access to the surgical site is gained by one or more portals and instruments used in the surgical procedure must be elongated to permit the distal ends of the instruments to reach the surgical site. Surgical cutting instruments for use in closed surgery are commonly referred to as "shavers" or "blades" and comprise an assembly composed of a rotatable inner member situated within a non-rotatable outer member. Such shavers conventionally have an elongated outer tubular member terminating at a distal end having an opening in the side and/or end wall to form a cutting port or window. An elongated inner tubular member is concentrically disposed in the outer tubular member and has a distal end disposed adjacent the opening in the distal end of the outer tubular member. The distal end of the inner tubular member has a surface or edge for engaging tissue via the opening in the distal end of the outer tubular member and in many cases cooperates with the opening to shear or cut tissue. The inner and outer tubular members both have hubs at their proximal ends to enable the shaver blade assembly to be attached to a handpiece to facilitate manipulation of the shaver blade as well as to provide power to the inner tubular member so it can be rotatably driven at its proximal end. The drive mechanism is normally a small electric motor situated in the handpiece and controlled by a foot switch, a finger actuated switch on the handpiece or switches on a console supplying power to the handpiece. The distal end of the inner tubular member can have various configurations depending upon the surgical procedure to be performed and the opening of the distal end of the outer tubular member has a configuration to cooperate with the particular configuration of the distal end of the inner tubular member. Cut tissue and irrigating fluid are aspirated through the hollow lumen of the inner tubular member to be collected via a tube communicating with the handpiece.

In such instruments, the cutting window at the distal end of the outer member is often fixed at a given angular orientation relative to the handpiece. The hub at the proximal end of the outer member is keyed to fit in a receiving collet having a keyway facing in only a particular orientation which necessarily causes the cutting window to face in a predetermined direction. The choice of where to position the keyway relative to other features on the handpiece is made during manufacture. However, in certain surgical procedures the surgeon may prefer to have the cutting window face in different directions relative to the handpiece, particularly if the handpiece has control switches or is shaped in a way which interferes with its use in certain window orientations.

While some mechanisms are known by which the angular orientation of the cutting window is adjustable, such mechanisms are often cumbersome and are difficult to operate during the course of an endoscopic surgical procedure. One known cutting window orientation adjustment method involves simply providing multiple keyways (or bayonet locking mechanisms), removing the shaver blade and reinserting the hub into the collet in a different position. Another known method utilizes a single keyway to fix the window relative to the collet and means to enable the collet itself to be unlocked and turned without removing the blade. This method, utilized for example on a APS High Speed Arthrotome manufactured by Hall Surgical, Carpinteria, Calif., requires a procedure in which the handpiece body and collet are each held, moving the collet distally a certain distance relative to the body, turning the collet to orient the window as desired and then releasing the collet to lock it in place relative to the body. While not necessarily detrimental in an open surgical procedure, this type of adjustment may in some instances be awkward to perform during the course of an arthroscopic procedure. An easier window orienting mechanism would be desirable.

While the ability to select the cutting window orientation is desirable, doing so with existing shaver blades destroys the blade recognition feature utilized in many arthroscopic shaver systems. This feature relies on encoding the blades with discrete magnets embedded in the hub of the outer tubular member and reading the position of these magnets with sensors in the handpiece. This information is used to control the speed of the drive motor and to perform other identification functions understood by those skilled in the art. Rotating the outer tubular member in order to orient the cutting window moves the magnets in the hub away from the sensors, thus providing inaccurate information to the control system operating the handpiece. It would be desirable to have the ability to orient the cutting window of a shaver blade without compromising the ability of the control system to read the code associated with the blade in use.

The ability to control the orientation of the cutting window should be considered in conjunction with the necessity for the surgeon to control the degree to which irrigating fluid and tissue debris is aspirated from the surgical work site. This is generally accomplished by providing the surgeon with a handpiece having an easily accessible aspiration control valve. Thus, the surgeon could hold the handpiece comfortably with the aspiration control button in a selected orientation while being able to orient the cutting window as desired. While aspiration controls for shaver blade handpieces are known, they are often either expensive to manufacture or difficult to use because the design of these controls is greatly dependent upon the manufacturing process utilized for the body of the handpiece. For example, one known finger activated suction control valve utilizes a single, longitudinally extending lever pivoted at the surface of an elongated handpiece about an axis perpendicular to the longitudinal axis of the handpiece. The lever is rotatable in a plane parallel to the axis. Another example utilizes a similar lever near the distal end of the handpiece but pivoted about an axis parallel to the longitudinal axis of the handpiece. This lever is rotatable in a plane perpendicular to the axis. In each of these examples the user must employ a side-to-side, lateral type of finger motion to manipulate the suction control valve.

Many surgeons prefer a suction control valve having an ergonomically more normal motion such as a forward/backward, longitudinal type of finger motion particularly if the handpiece is small and held like a pencil. One known forward/backward valve is in the form of a lever extending outwardly from the axis of the handpiece, the radially inner end of the lever attached to a rotatable apertured plug situated in a transverse channel drilled through the distal end of an axially aligned aspiration channel in a handpiece. The plug has a bore which, by rotation of the plug about its axis, is aligned in either an open or closed position by the forward/backward motion of the lever. Known handpieces having such a transverse control valve are expensive and difficult to manufacture.

Prior art surgical shaver handpieces are generally machined from bar stock in view of the desire to minimize the number of throughbores and openings which must be sealed. This necessitates the use of the aforementioned transverse aspiration control valves. Even in those instances where handpieces have a main throughbore for the motor, blade, etc. and another parallel throughbore for the aspiration channel, the aspiration control valves are only laterally adjustable.

It is consequently an object of this invention to produce a surgical shaver handpiece having a simplified longitudinally actuable aspiration control valve which is less costly and difficult to manufacture than known units.

It is another object of this invention to produce a surgical shaver handpiece in which aspiration control may be achieved by a longitudinally movable slide switch.

It is yet another object of this invention to produce a surgical shaver handpiece having a simplified longitudinally actuable aspiration control valve with a combination seal/bearing unit to support and seal the valve.

It is also an object of this invention to produce a surgical shaver handpiece in which the orientation of the cutting window of the outer member is easily adjustable without disengaging the blade from the handpiece.

It is yet another object of this invention to produce a surgical shaver handpiece in which the orientation of the cutting window may be changed while retaining the ability of the control system to read the code associated with the blade in use in any window orientation.

SUMMARY OF THE INVENTION

These and other objects of this invention are achieved by the preferred embodiment disclosed herein which is a surgical instrument for driving an elongated surgical tool having an inner member rotatably situated within an outer member, the outer member having a cutting window facing at least partially in a direction transverse to the axis. The instrument comprises a housing with a drive means within the housing to drive the inner member of the tool. A releasable collet means at the distal end of the housing receives the surgical tool and holds it longitudinally fixed relative to the drive means. The collet means is adapted to receive the outer member of the tool in a predetermined angular orientation relative to the axis of the housing. A rotation enabling means is provided for enabling rotation of the collet means in order to vary the predetermined angular orientation of the outer member. The rotation enabling means comprises a detent means to retain the collet in a selected position, the detent means being manually rotatable without being first manually urged longitudinally. The detent means comprises a first locking plate having a first locking surface facing in a distal direction and a second locking plate having a second locking surface facing in a proximal direction. The first and second locking surfaces engage each other to prevent relative rotation between the first and second locking plates. A hollow, outer cylindrical collet member is fixedly secured to the first locking plate and has a keyway for fixing the position of the outer member. A spring means is interposed between the outer collet member and the second locking plate for selectively maintaining the first and second locking surfaces in engagement.

The invention is also embodied in an elongated surgical handpiece having a body with a proximal end and a distal end and the method of manufacturing same. The handpiece has a longitudinally aligned first bore extending between the proximal end and the distal end for containing a motor for driving a surgical instrument and a longitudinally aligned second bore, parallel to the first bore, for providing an aspiration conduit for aspirating material from the distal end to the proximal end. The method comprises the steps of providing an extrudable material, extruding the extrudable material with the first and second bores extending through the body and forming an oblique aspiration channel extending from said second bore distally to said first bore. The method further comprises providing a longitudinally movable aspiration control valve having an elongated pin sized to be axially received in the distal end of the second bore and sufficiently elongated to selectively occlude the oblique aspiration channel. A slide body is adapted to slidably retain the pin within the second bore and to seal the distal end of the second bore.

The invention is also embodied in a surgical instrument for driving a rotatable surgical tool, the instrument comprising a housing having a drive means for driving the tool and a releasable collet means for receiving the tool and holding it fixed to the drive means. The collet means is adapted to receive the tool in a predetermined angular orientation relative to the housing. The instrument has a means for enabling rotation of the tool to vary the predetermined angular orientation and a recognition means for identifying the tool regardless of its angular orientation relative to the housing.

BRIEF DESCRIPTION OF THE DRAWINGS

FIGS. 7a, 7b and 7c are side elevation views of the collet subassembly shown in FIG. 4 in various stages of assembly.

FIGS. 13a and 13b are side and front elevation views, respectively, of a locking ring component shown in FIG. 7a.

DESCRIPTION OF THE PREFERRED EMBODIMENT

Figure 1:
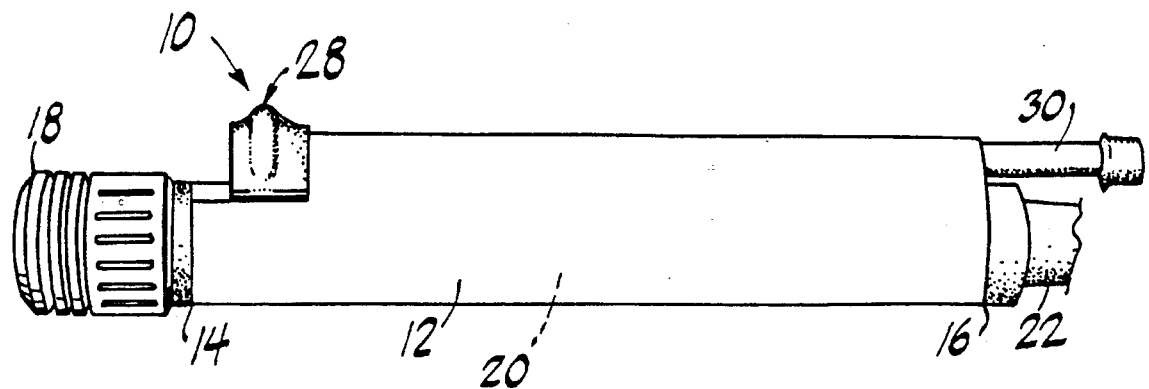
FIG. 1 is a side elevation view of a surgical shaver handpiece constructed in accordance with the principles of this invention.
Figure 2:
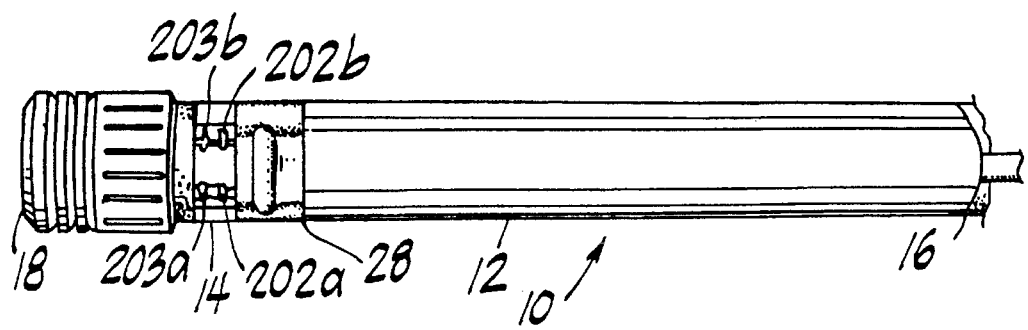
FIG. 2 is a top view of FIG. 1 showing the slide aspiration control valve in a fully closed, proximal-most position.
Figure 3:
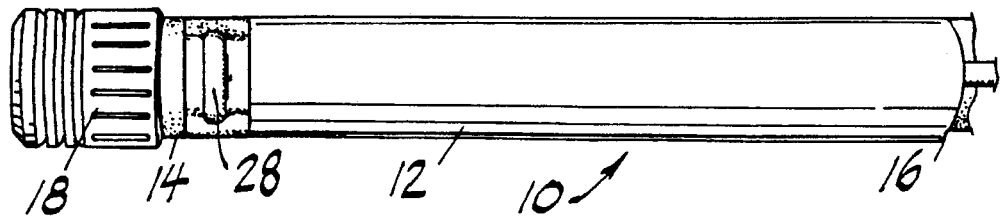
FIG. 3 is a top view of FIG. 1 showing the slide aspiration control switch in a fully open, distal-most position.
Figure 4:
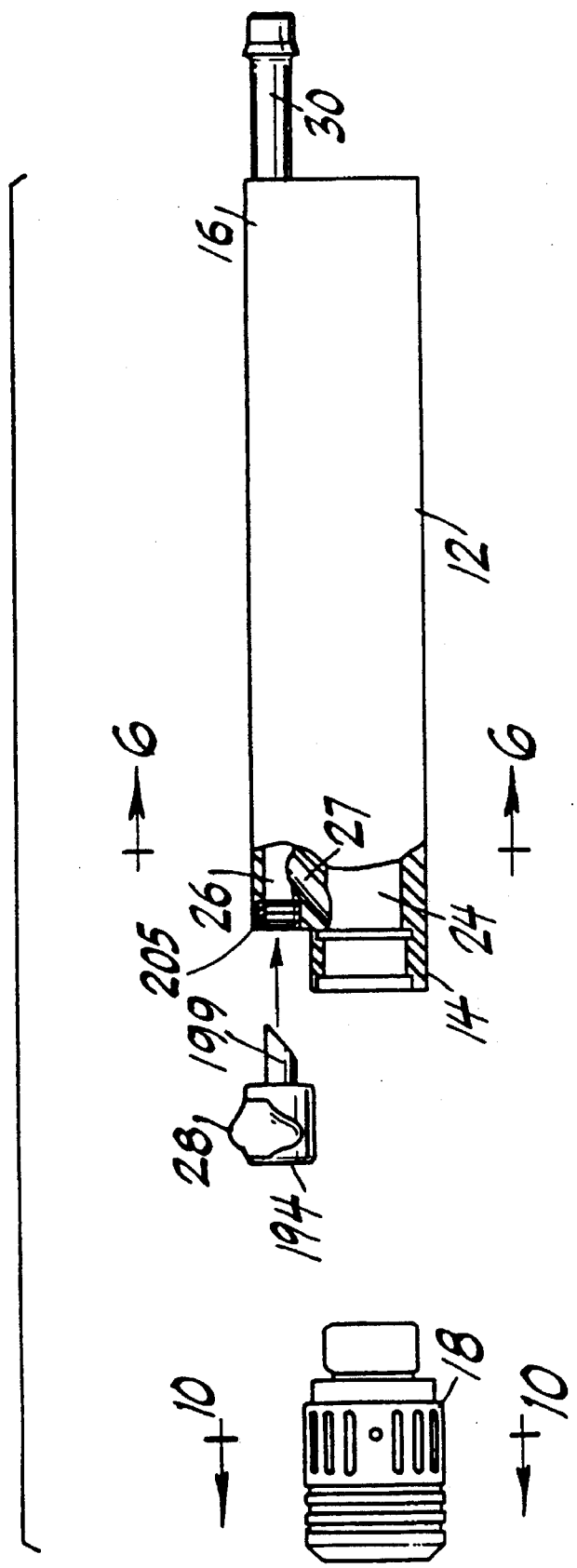
FIG. 4 is an exploded partially cross-sectional view of FIG. 1.
Figure 5:
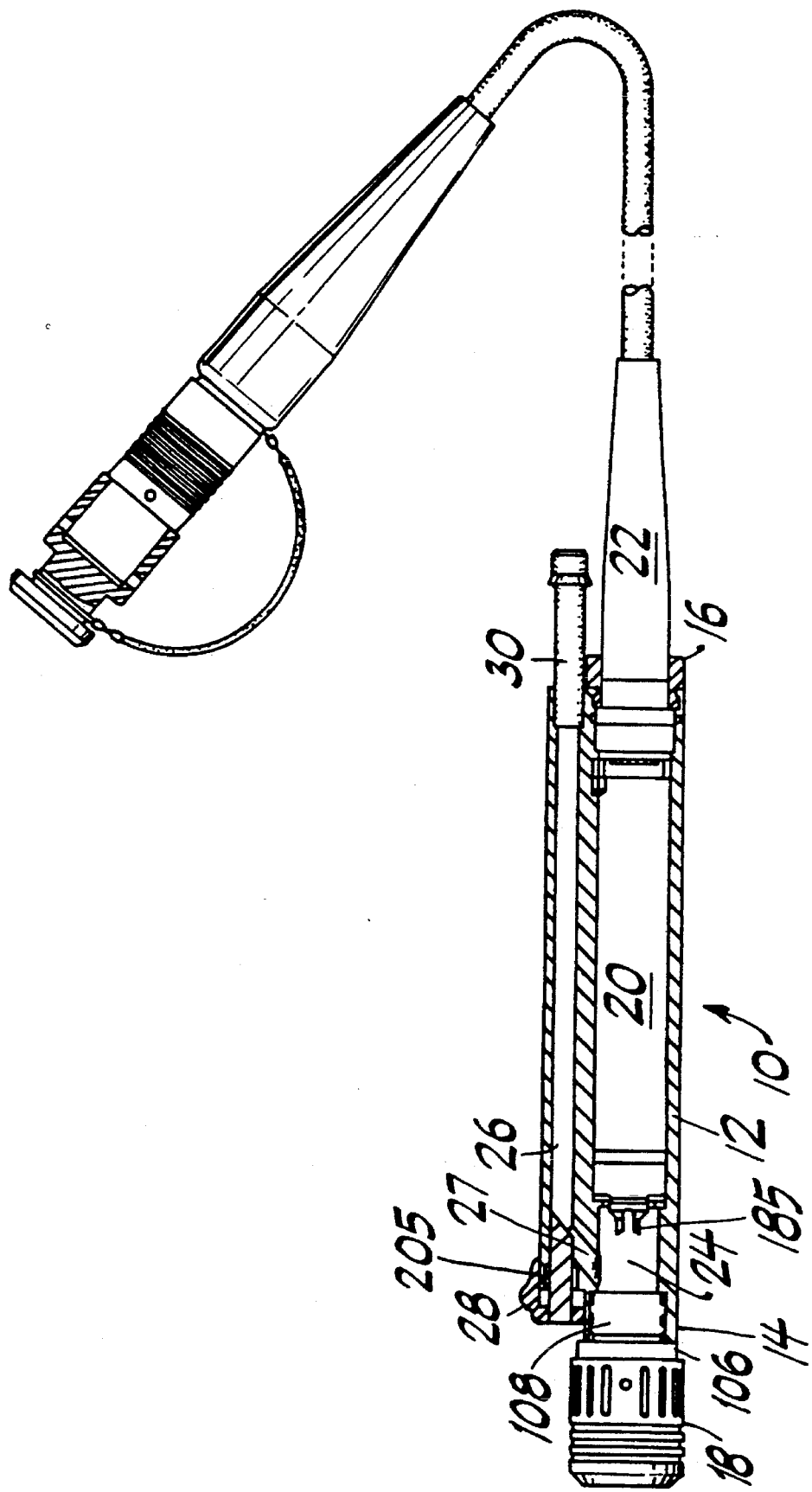
FIG. 5 is an assembled partially cross-sectional elevation view of FIG. 1.
Figure 6:
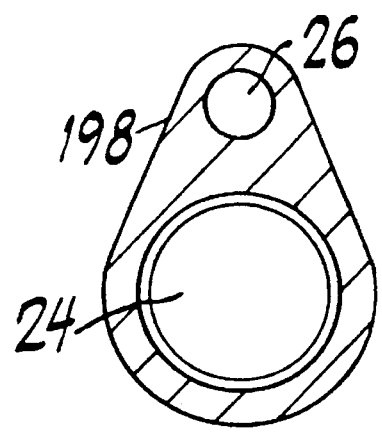
FIG. 6 is a cross-sectional view of FIG. 4 taken along the lines 6—6.

Referring now to FIGS. 1 through 5 there is shown a surgical shaver handpiece 10 constructed in accordance with the principles of this invention. Handpiece 10, constructed in a modular fashion to facilitate its assembly and repair, comprises a body 12 having a distal end 14, a proximal end 16, a collet assembly 18, a motor/seal assembly 20 and a cable assembly 22. As best seen in FIGS. 5 and 6, body 12 has two parallel, longitudinally extending throughbores: bore 24 is the main channel for receiving the motor/seal assembly 20 and collet assembly 18 and bore 26 is an aspirating channel which is provided with a slidable suction control valve 28 at the distal end 14 of body 12 and a tubing adapter 30 at the proximal end 16. An oblique aspiration communication channel 27 extends distally from bore 26 to bore 24.

As best seen in FIG. 6, body 12 has a tear-drop shape which, in the preferred embodiment, is formed by extruding an extrudable material (aluminum, plastic, etc.) with throughbores 24 and 26. Oblique channel 27 and the annular grooves, threads and internal component receiving channels must be machined into body 12 after the extrusion step, but these are relatively minor manufacturing steps which are also employed in prior art non-extruded units. All known prior art handpieces are more expensive and time consuming to produce because they are machined entirely from a single bar of material. An additional advantage to extrusion is that, as will be understood below, it facilitates the use of a simplified slide aspiration control valve 28.

Figure 7A:
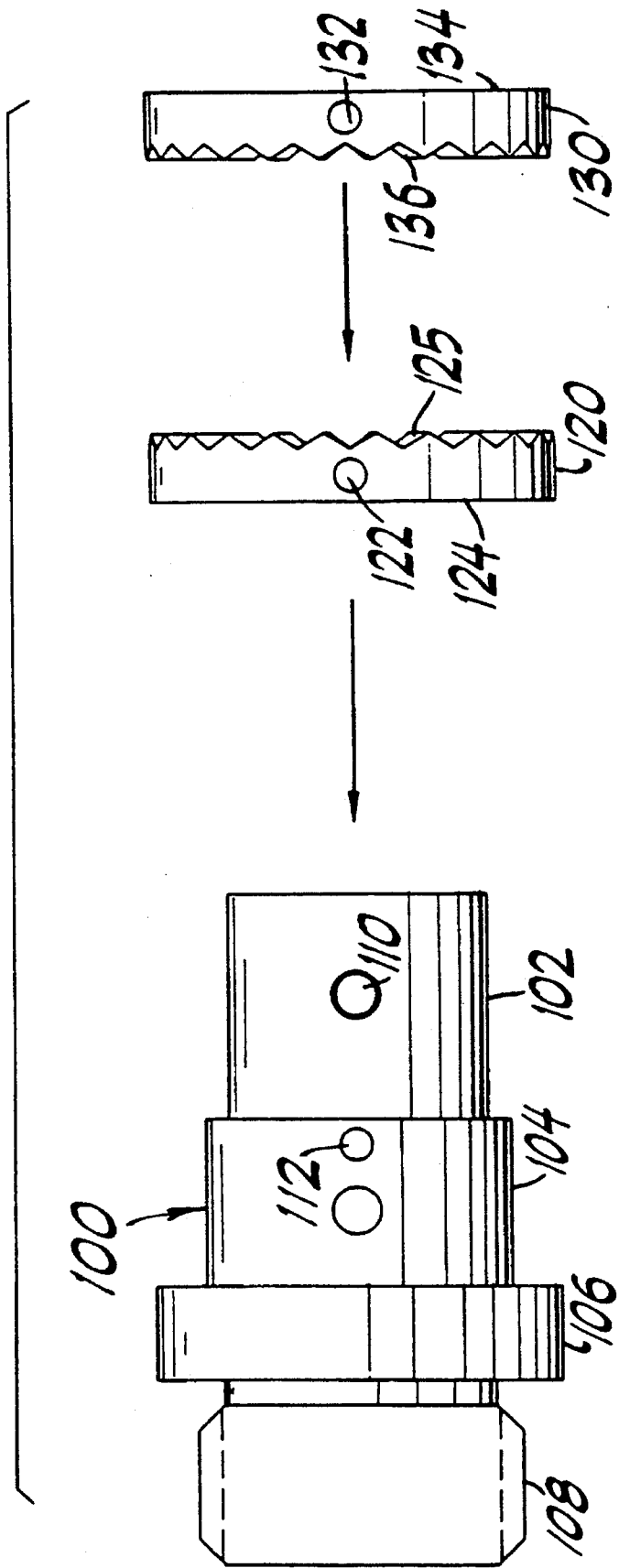

The rotatable self-locking collet mechanism in handpiece 10 comprises collet assembly 18 which is shown in more detail in FIGS. 7a, b and c. As will be understood below, collet assembly 18 serves to secure handpiece 10 to a shaver blade assembly, best seen in FIG. 14.

Collet inner body 100 is formed from an integral, hollow piece of material having a distal cylindrical portion 102, an intermediate cylindrical portion 104, a shoulder 106 and a proximal threaded portion 108. Cylindrical portion 102 is provided with three ball detents 110 equally spaced around the periphery of cylindrical portion 102 (only one ball detent is shown in FIG. 7a). Cylindrical portion 104 is provided with three pin receiving apertures 112 (only one of which is shown) equally spaced around the periphery of cylindrical portion 104, the purpose of which will be explained below. Shoulder 106 is sized to smoothly abut collet body 100 against the distal opening 14 of handpiece body 12. Cylindrical threaded portion 108 is received in distal end 14 and secures the mounting of collet assembly 18 to handpiece body 12.

Locking plate 120, best seen in FIGS. 7 and 13, is an annular ring having three equally spaced pin receiving apertures 122, a smooth proximally facing rear surface 124 and a toothed distally facing front surface 126. Locking ring 120 has an internal aperture 128 having a diameter sufficient to enable it to slide along intermediate cylindrical portion 104. An identical locking ring 130 is provided with three pin receiving apertures 132, a distally facing rear surface 134 and a proximally facing front surface 136. The central aperture of locking ring 130 is also sized to be received on intermediate portion 104 although locking ring 130 is fixed to portion 104 by pins 113 inserted through pin apertures 132 and into apertures 112, as best seen in FIG. 8.

Figure 7B:
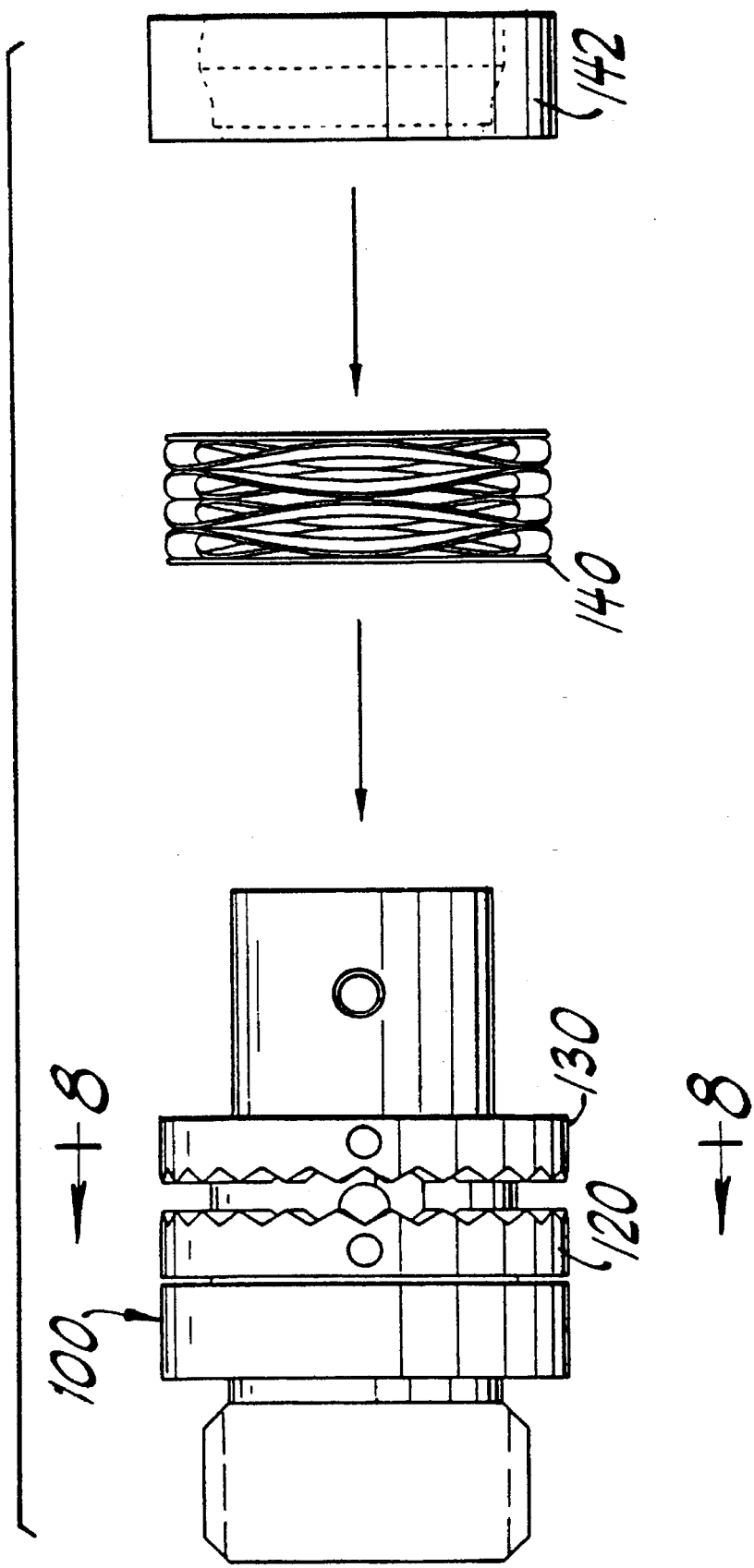
Figure 8:
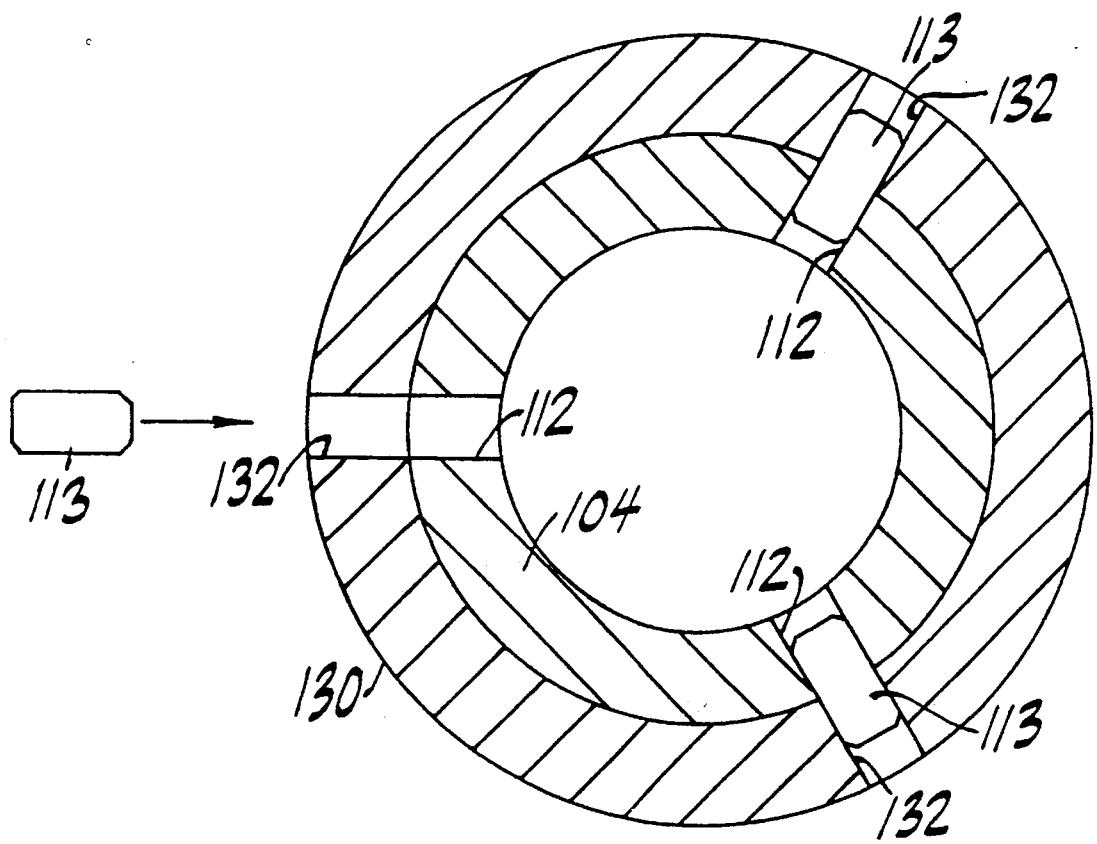
FIG. 8 is a cross-sectional view of FIG. 7b taken along the line 8—8.
Figure 9:
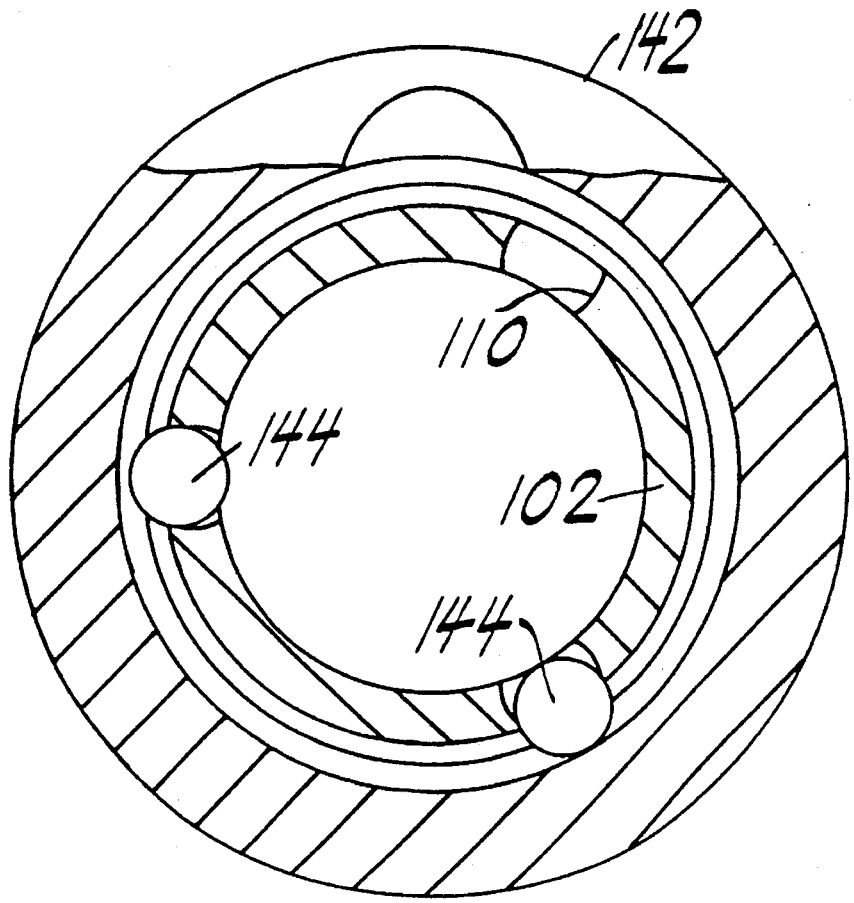
FIG. 9 is a cross-sectional view of FIG. 7c taken along the line 9—9.
Figure 10:
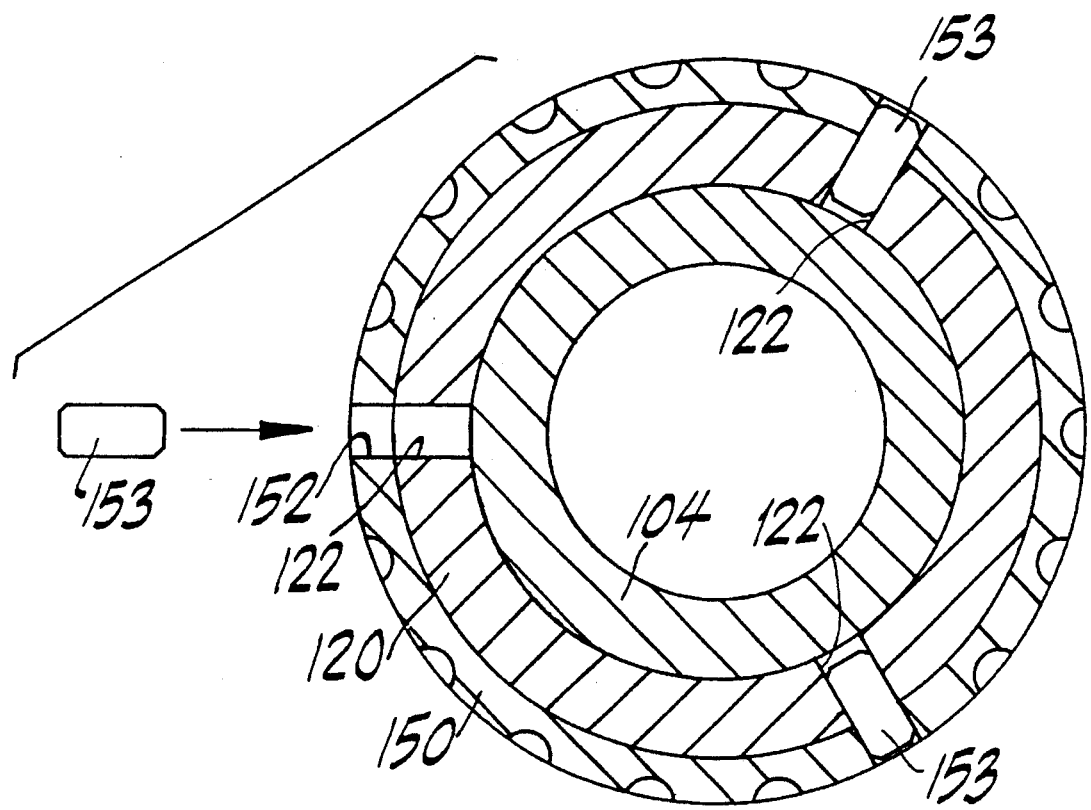
FIG. 10 is a cross-sectional view of FIG. 4 taken along the line 10—10.

As shown in FIG. 7b, once locking rings 120 and 130 are assembled onto collet body 100, a cylindrical pre-loading spring 140, sized to be received on cylindrical portion 102, is abutted against the distally facing rear surface of locking ring 130 and ball retaining ring 142 is then abutted against the distally facing side of spring 140. Balls 144 are then inserted into ball detents 110 as shown in FIGS. 7c and 9 and the entire assembly is held together by hollow, cylindrical outer collet body member 150 which is pinned via pin 153 to three equally spaced pin receiving apertures 152 to corresponding apertures 122 in locking ring 120, as best seen in FIG. 10. Pre-loading spring 140 serves to cam balls 144 into the locked position and also to urge locking plate 120 against locking plate 130 (note they are spaced in FIG. 7c for clarity). Thus, it will be understood that while outer collet body 150 is normally biased distally by spring 140, thereby causing the toothed surfaces of locking rings 120 and 130 to engage, collet body 150 may be caused to move rearwardly (proximally) in the direction of arrow A by mere rotation. The mechanical advantage of the locking rings allows direct turning of the outer collet body without pulling it proximally or pushing it distally. It will be understood that turning the collet body 150 causes the facing front surfaces of the locking rings to disengage, thereby enabling relative rotation of the locking rings.

Figure 12:
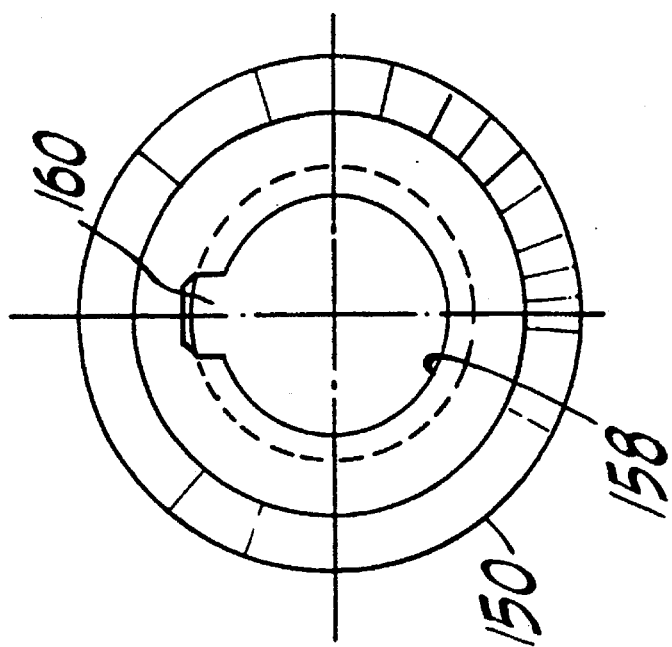
FIG. 12 is a right end view of FIG. 11.
Figure 11:
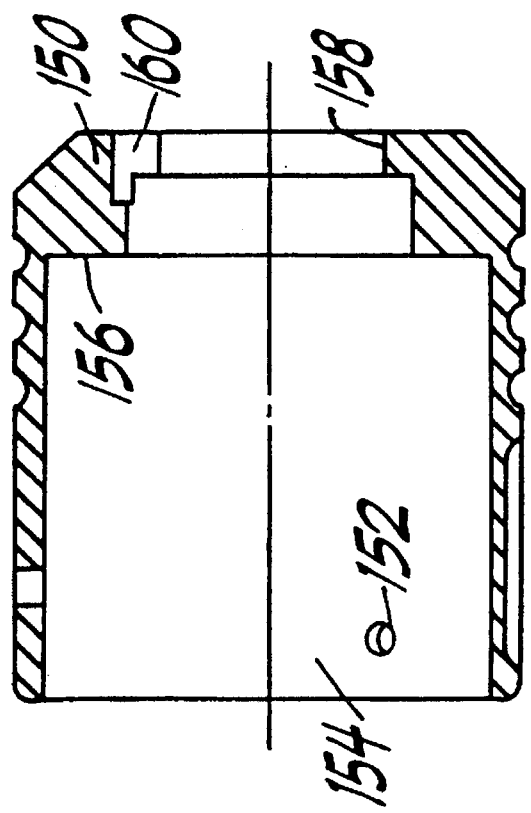
FIG. 11 is a cross-sectional elevation view of a portion of the collet subassembly of FIG. 7c.
Figure 14:
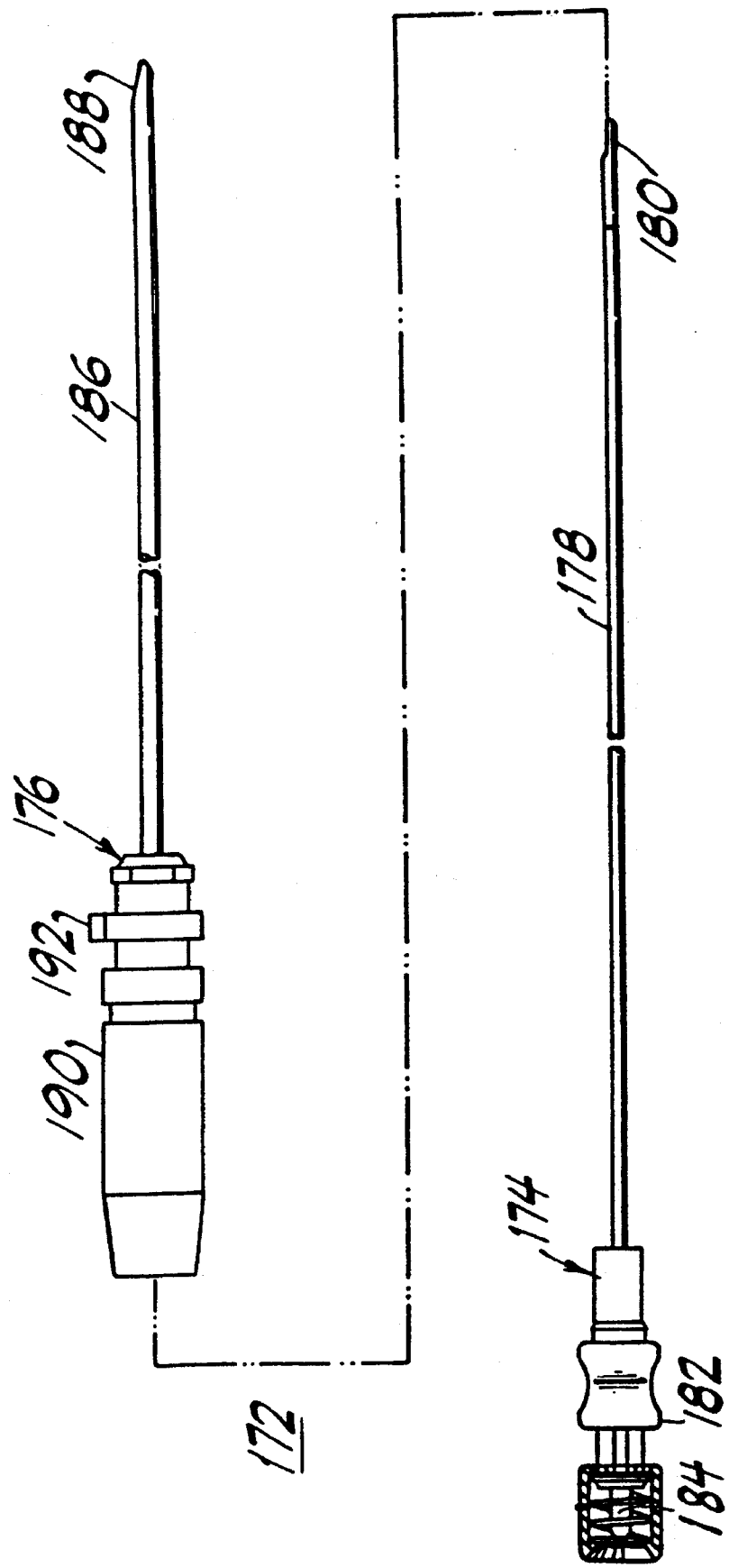
FIG. 14 is an exploded side elevation view, partially in cross-section, of a shaver blade for use with the handpiece of FIG. 1.

Outer collet body 150, best seen in FIGS. 11 and 12, has a hollow interior 154 and an internal shoulder 156 which engages the distal side of ball retainer 142. A distal axially aligned aperture 158 is sized to receive a shaver blade assembly and is provided with a keyway 160 adapted to engage a corresponding key 192 on a shaver blade 172 best seen in FIG. 14. Referring briefly to FIG. 14, shaver blade assembly 172 comprises an elongated inner blade 174 and an elongated outer blade 176. Inner blade 174 comprises an elongated tubular member 178 having a cutter 180 at its distal end and a hub 182 at its proximal end. Hub 182 includes a drive tang 184 to engage drive connection 185 of motor/seal assembly 120 (best seen in FIG. 5) to drive the inner member. Outer blade 176 comprises an elongated tubular member 186 having a cutting window 188 at its distal end and a hub 190 at its proximal end. Hub 190 includes a key tang 192 which fits into the keyway of the outer collet body member.

Figure 13B:
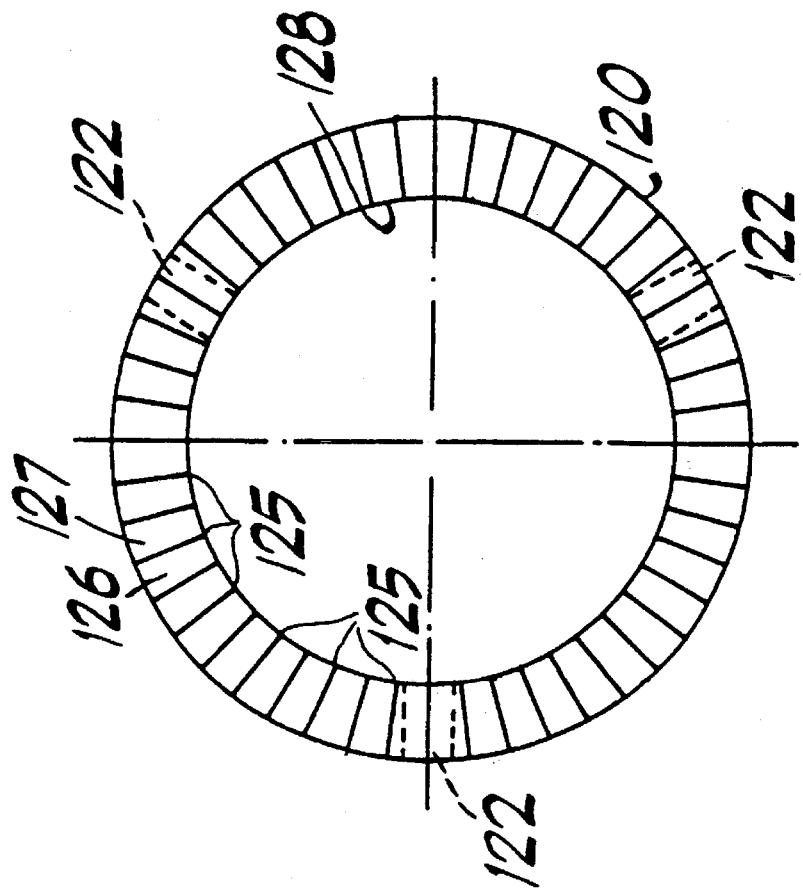
Figure 13A:
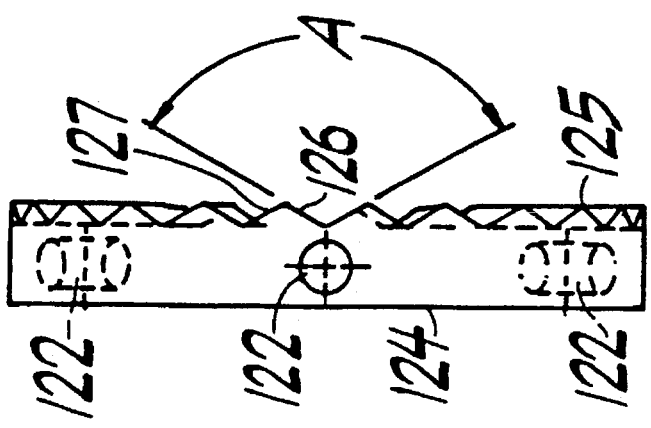

Referring to FIGS. 13a and 13b, a detailed view of locking ring 120 shows that it has a central aperture 128 and a plurality of annularly arranged shallow teeth 125. The sides 126, 127 of adjacent teeth are separated by angle A which in the preferred embodiment is on the order of 119°. The shallow design of the teeth enables the locking rings to be easily rotated relative to one another without first having to push outer collet body longitudinally rearwardly to disengage the teeth. The teeth of one locking ring slide along the teeth of the other locking ring merely by manually rotating the outer collet body. The annular array of 24 teeth enables the collet to be adjustable throughout 360° in increments of 15°.

Figure 16:
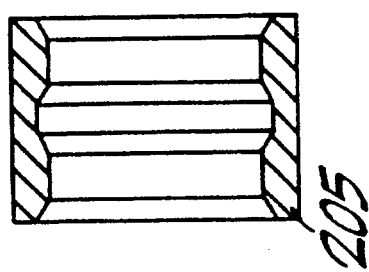
FIG. 16 is a side elevation view in cross-section of a seal/bearing used in the aspiration control slide valve shown in FIGS. 15a and 15b.
Figure 15A:
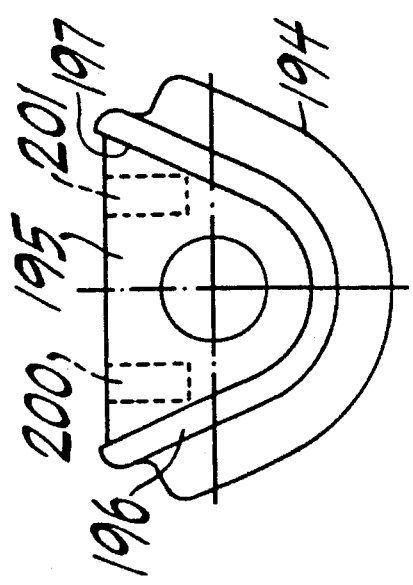
FIGS. 15a and 15b are end and cross-sectional views of an aspiration control slide valve constructed in accordance with the principles of this invention.
Figure 15B:
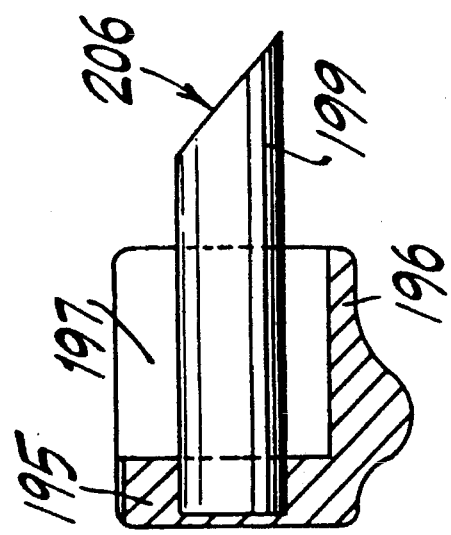

A slide aspiration control valve 28, best seen in FIGS. 1, 4, and 15a and 15b, comprises a three sided slide body 194 having an end wall 195, an arcuate side wall 196 which has an inner surface 197 shaped to conform to the arcuate outer surface 198 of body 12 adjacent channel 26 as best seen in FIG. 6. End wall 195 has a pin 199 extending perpendicularly therefrom, pin 199 adapted to engage the distal end of throughbore 26 as best seen in FIG. 5. End wall 195 is provided with a pair of apertures 200 and 201 to receive pre-loaded springs (not shown) for maintaining the slide body in position in detent pairs 202a, 202b and 203a and 203b formed into the top of body 12. A combination cylindrical seal/bearing 205, best seen in FIG. 16, is situated at the distal end of bore 26 and cooperates with pin 199 to seal bore 26. Pin 199 is slidable in seal/bearing 205 has an oblique end face 206 and oriented in alignment with oblique channel 27 to facilitate the flow of aspirated fluid from bore 24 through oblique channel 27 to bore 26. It will be understood that the various positions of slide 28 in FIGS. 1, 2 and 3 correspond to various degrees of opening of the port or aperture formed by the intersection of channels 26 and 27.

Figure 17:
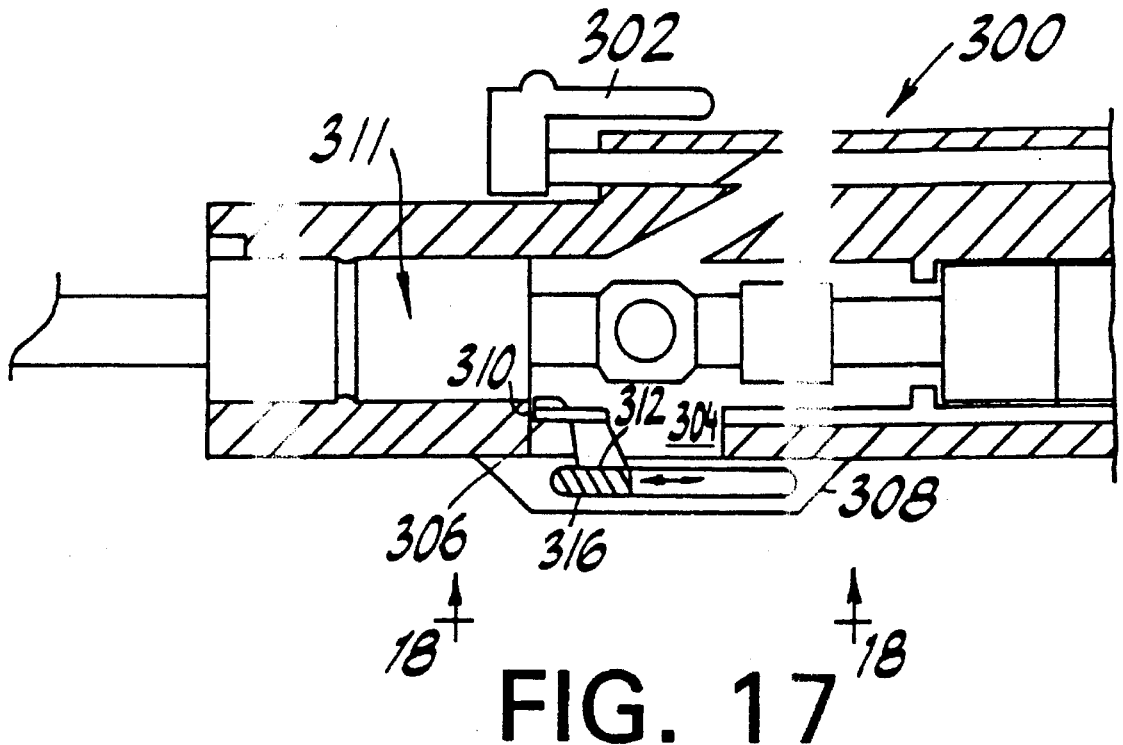
FIG. 17 is a cross-sectional view of the distal end of an alternate embodiment of a surgical shaver handpiece having a blade recognition feature.
Figure 18:
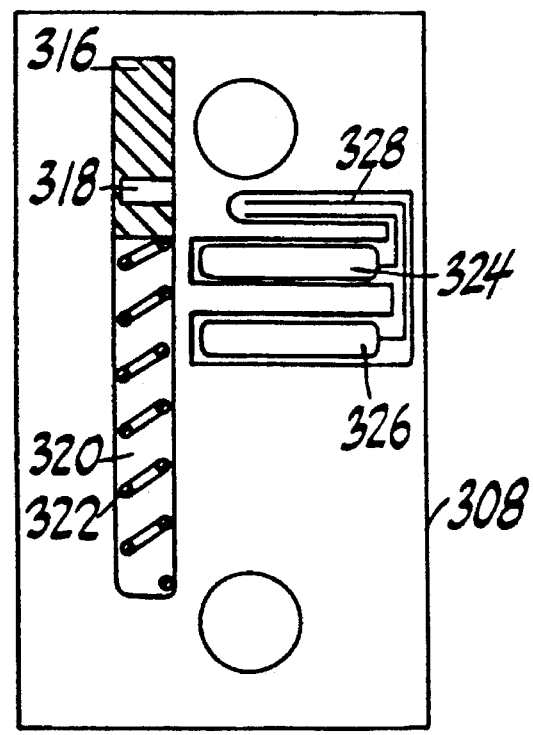
FIG. 18 is a diagrammatic plan view of FIG. 17 taken along the line 18—18.

FIGS. 17 and 18 show an alternate embodiment of the invention in which a shaver blade handpiece is provided with a blade recognition feature suitable for identifying a coded blade in all angular positions relative to the housing. Handpiece 300 is identical to handpiece 10 in all respects other than the structure of the distal end 302 related to blade recognition. The distal end 302 of handpiece 300 is provided with an aperture 304 in its side wall through which a hub pick-up lever 306 extends inwardly. Hub pick-up lever 306 is attached to the bottom of a sliding magnet carrier 316 held within housing 308 secured to the outside of housing 300. Hub pick-up lever 306 has a distal end 310 situated internally within handpiece 300 in order to contact the proximal end of outer hub 311 of a blade assembly. Hub pick-up 306 is attached at its proximal end 312 to magnet carrier 316 which supports a magnet 318 and slides within a longitudinally extending channel 320 in magnet housing 308 against the bias of spring 322. Also situated in magnet housing 308 are reed switches or Hall sensors 324 and 326 which are spaced longitudinally along channel 320. It will be understood that as hub pick-up 306 is longitudinally moved to varying degrees by its interaction with the proximal end of the outer hub of a blade assembly, the magnet 318 will be placed proximally to either switch/sensor 324, switch/sensor 326 or beyond. The position of magnet 318 relative to switches/sensors 324 and 326 represents the code identifying the particular blade assembly, which code may be defined and communicated via wires 328 to a control console (not shown). The particular embodiment described in FIGS. 17 and 18 requires the length of the outer hub 311 of each blade assembly to vary as a function of the code to be associated with a particular blade assembly.

Figure 19:
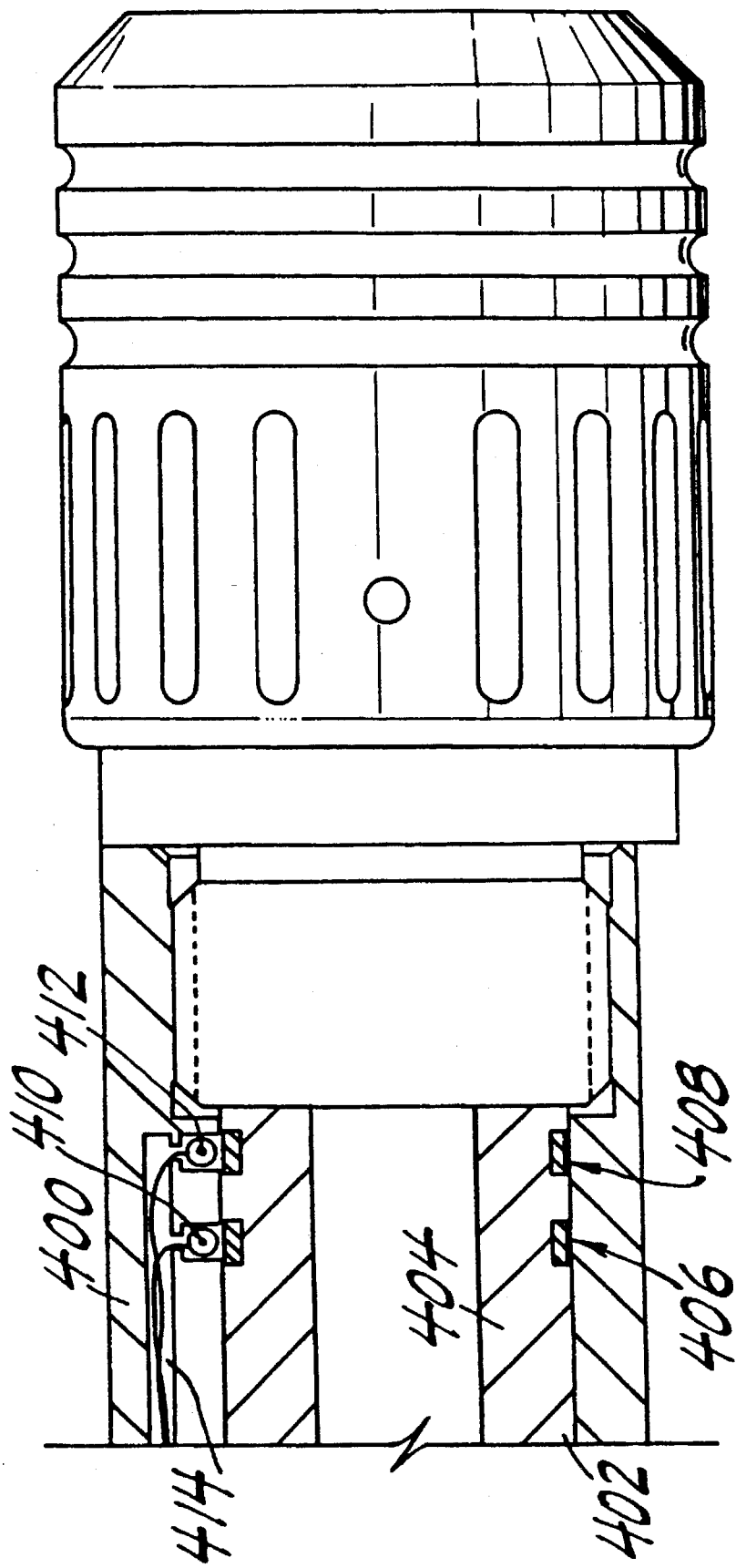
FIG. 19 is a diagrammatic side elevation view, partly in cross-section, of another alternate embodiment of a surgical handpiece having a blade recognition feature.

Yet another alternative embodiment of a blade recognition system is shown in FIG. 19 wherein an annular indicator is situated on the exterior surface of the hub of a blade assembly. Such an annular indicator would be longitudinally fixed and would be recognized by an associated sensor fixed within the housing of the handpiece regardless of the angular orientation of the outer hub to the handpiece. This arrangement would not require changes in the lengths of the hubs of the outer tubular members from one type of blade to the next. The code would be represented by the presence or absence of the annular indicator in the annular band sensed by a particular sensor on the housing. In FIG. 19, only the distal end of handpiece 400 is shown in engagement with the proximal end 402 of a blade assembly (not shown) having an outer hub 404. The unpictured portions of handpiece 400 and the blade assembly are identical to similar components previously discussed and need not be further described. Hub 404 comprises annular indicators 406 and 408 spaced longitudinally along the external surface of hub 404. Housing 400 has sensors 410 and 412 situated in proximity to the positions that annular indicators 406 and 408, respectively, will be in when hub 404 is fully seated in the handpiece. Sensors 406 and 408 are connected in a conventional manner by wires 414 to a control system. The number and spacing of the annular indicators may be varied provided there is a sensor situated to sense the presence or absence of an indicator at a defined position on the hub. For example, an array of any number of sensors similar to 410 and 412 could be provided to read the code defined by the presence or absence of annular indicators in any of the positions corresponding to (i.e. proximate) to the sensors. If annular indicators 406 and 408 are magnetic (for example, flexible magnetic strips or more rigid annular magnets) the sensors 410, 412 could be reed switches or Hall sensors. If indicators 406, 408 are metal rings, sensors 410, 412 could be eddy current sensors. If an annular indicator other than a magnet or metal is used, for example, a light reflective surface, the sensor would necessarily be receptive to emanations from the indicator. One example of such an annular non-magnetic, non-metallic indicator may include an annular band on the surface of hub 404 which may contain an optically readable code. The code, repeated about the periphery, could be illuminated by a light source in the handpiece and the reflected light could be detected by a detector properly positioned in the handpiece.

It will be understood by those skilled in the art that numerous improvements and modifications may be made to the preferred embodiment of the invention disclosed herein without departing from the spirit and scope thereof.

What is claimed is:

1. A method of manufacturing an elongated surgical handpiece having a body with a proximal end, a distal end, a longitudinally aligned first bore extending between said proximal end and said distal end for containing a motor for driving a surgical instrument, a longitudinally aligned second bore, parallel to said first bore, for providing an aspiration conduit for aspirating material from said distal end to said proximal end, said method comprising the steps of:

providing an extrudable material;

extruding said extrudable material to produce said body with said first and second bores extending therethrough;

forming an oblique aspiration channel extending from said second bore distally to said first bore;

providing a longitudinally movable aspiration control valve comprising an elongated pin sized to be axially received in the distal end of said second bore and sufficiently elongated to selectively occlude said oblique aspiration channel, a slide body adapted to slidably retain said pin within said second bore and a handle means for enabling a user to longitudinally move said slide body;

sealing the distal end of said second bore with said aspiration control valve.

2. A method according to claim 1 wherein said control valve is linearly actuable in a direction aligned with the longitudinal axis of said surgical handpiece.

* * * * *